(12) United States Patent
Egorov (10) Patent No.: US 9,861,316 B2
(45) Date of Patent: Jan. 9, 2018

(54) METHODS AND PROBES FOR VAGINAL TACTILE AND ELECTROMYOGRAPHIC IMAGING AND LOCATION-GUIDED FEMALE PELVIC FLOOR THERAPY

(71) Applicant: Vladimir Egorov, Princeton, NJ (US)

(72) Inventor: Vladimir Egorov, Princeton, NJ (US)

(73) Assignee: Advanced Tactile Imaging Inc., Ewing, NJ (US)

( * ) Notice: Subject to any disclaimer, the term of this patent is extended or adjusted under 35 U.S.C. 154(b) by 0 days.

(21) Appl. No.: 15/248,268

(22) Filed: Aug. 26, 2016

(65) Prior Publication Data

US 2017/0065222 A1   Mar. 9, 2017

Related U.S. Application Data

(60) Provisional application No. 62/214,042, filed on Sep. 3, 2015.

(51) Int. Cl.
*A61B 5/00* (2006.01)
*A61N 1/05* (2006.01)
(Continued)

(52) U.S. Cl.
CPC .......... *A61B 5/6847* (2013.01); *A61B 5/0035* (2013.01); *A61B 5/04882* (2013.01);
(Continued)

(58) Field of Classification Search
CPC ... A61B 5/6847; A61B 5/04882; A61B 5/227; A61B 5/4337; A61N 1/0524; A61N 1/36007

See application file for complete search history.

(56) References Cited

U.S. PATENT DOCUMENTS 8,052,622 B2   12/2011   Egorov
8,187,208 B2   5/2012    Egorov
(Continued)

OTHER PUBLICATIONS

Egorov V, van Raalte H, Lucente V, Sarvazyan A. Biomechanical characterization of the pelvic floor using tactile imaging. Chapter 16 in Biomechanics of the Female Pelvic Floor, Elsevier, p. 317-348, 2016.

*Primary Examiner* — Eric D. Bertram
(74) *Attorney, Agent, or Firm* — Boris Leschinskuy (57) ABSTRACT

Methods and a probes are disclosed for vaginal tactile and electromyographic imaging, and location-guided female pelvic floor therapy. Methods include the steps of inserting a vaginal probe equipped with tactile sensors and electrodes acting as electromyographic sensors into a vagina along a vaginal canal to separate apart two opposing vaginal walls, recording a tactile response and an electromyographic response from at least one of two opposing vaginal walls during pelvic floor muscle contraction, determining locations along the vaginal canal for delivery of therapy based on presence of tactile response above a predetermined tactile threshold and/or presence of electromyographic response above a predetermined EMG threshold along the vaginal probe, selecting at least one of target locations to be used for location-guided therapy, and applying the therapy such as electrical muscle stimulation to at least one of selected locations using the same electrodes at these locations. The probe comprises a probe housing, a tactile sensors array, a plurality of electrodes which can be used as an electromyography array or as an electric muscle stimulation array, and at least one reference electrode.

10 Claims, 4 Drawing Sheets

(51) Int. Cl.
*A61N 1/36* (2006.01)
*A61B 5/0488* (2006.01)
*A61B 5/22* (2006.01)
*A61B 5/06* (2006.01)

(52) U.S. Cl.
CPC .............. *A61B 5/065* (2013.01); *A61B 5/227* (2013.01); *A61B 5/4337* (2013.01); *A61B 5/6885* (2013.01); *A61N 1/0524* (2013.01); *A61N 1/36007* (2013.01)

(56) References Cited

U.S. PATENT DOCUMENTS

| | | | |
|---|---|---|---|
| 8,419,659 B2 | 4/2013 | Egorov | |
| 8,840,571 B2* | 9/2014 | Egorov | A61B 5/227 600/591 |
| 2009/0270963 A1* | 10/2009 | Pelger | A61B 5/04882 607/138 |
| 2016/0345817 A1* | 12/2016 | Calderon | A61B 1/32 |

* cited by examiner

METHODS AND PROBES FOR VAGINAL TACTILE AND ELECTROMYOGRAPHIC IMAGING AND LOCATION-GUIDED FEMALE PELVIC FLOOR THERAPY

CROSS-REFERENCE TO RELATED APPLICATIONS

This patent application claims a priority benefit from the U.S. Provisional Patent Application No. 62/214,042 filed Sep. 3, 2015 by the same inventor and with the same title. This provisional patent application is incorporated herewith by reference in its entirety.

GOVERNMENT-SUPPORTED RESEARCH

This invention was made with the US Government support under grant No. R43AG053935 awarded by the National Institute on Aging. The Government has certain rights in this invention.

FIELD OF THE INVENTION

The present invention generally relates to methods and devices for female pelvic floor imaging and treatment. Specifically, the invention describes methods and devices for providing vaginal tactile and electromyographic imaging and location-guided female pelvic floor therapy.

BACKGROUND

Urinary incontinence (UI) is defined as the complaint of any involuntary loss of urine. The most common type of UI is stress urinary incontinence (SUI), defined as the complaint of involuntary leakage on effort or exertion, or on sneezing or coughing. Overactive bladder (OAB) is a complex of symptoms that is characterized by urinary urgency, with or without urgency-associated UI. Both UI and OAB are more common in women than in men and their prevalence is increased with age. The UI affects up to 38% of women; while the OAB prevalence estimates are reaching 43%. These conditions are socially embarrassing, causing significant morbidity and quality of life impact.

The pelvic floor muscles (PFM) form the floor of the female pelvic basin and help maintaining continence by actively supporting the pelvic organs. In the older population, pelvic floor disorders represent the combination of neuro-urinary pathology, functional and cognitive impairments, and changing biomechanical conditions of tissues.

The female pelvic floor comprises the pelvic diaphragm muscles (pubococcygeus, puborectalis, and iliococcygeus, levator plate together known as the levator ani), pubovaginal and puboperineal muscles, urethral and anal sphincter muscles. Anatomically and functionally these muscle are interrelated with each other. Correct action of the pelvic floor muscles is described as a squeeze around the pelvic openings and an inward lift. The pelvic floor muscles function includes electrical signal transmission and a mechanical action (contraction). The pelvic floor disorders result from neuro-urinary pathology as well as muscle functional impairment due to changes in biomechanical properties of soft tissues with age. That is why pelvic floor muscles characterization and diagnosis must include biomechanical (force) measurements and electromyographic (EMG) measurements or better tactile and EMG imaging with improved spatial resolution.

The pelvic floor treatment options include surgery, sacral neuromodulation with implanted electrodes, electrical muscle stimulation, medications and physiotherapy. An invasive surgical approach is considered as the ultimate treatment. However, numerous patient reports of adverse events are associated with surgical mesh; these include vaginal extrusion, erosion, infection, pain, dyspareunia, lower urinary tract symptoms, recurrence of incontinence, urinary retention, and blood vessel injury. Implantation of electrodes for sacral neuromodulation is also considered an invasive procedure. Physical training and medications are often not effective for treatments of UI. The transvaginal electrical simulation demonstrated feasibility for UI and OAB treatments but lacks objective functional and anatomically-specific guidance to select precise location for the effective therapy. To date, there is no standardized, reproducible tool to accurately assess the pelvic floor muscles function in anatomically-specific manner, and to apply guided muscle stimulation for UI and OAB therapy.

Biofeedback with vaginal pressure measurements (air balloon or 1-2 pressure sensors) has been widely used in the treatment of pelvic floor dysfunctions, mainly by promoting patient learning about muscle contraction. However, its effectiveness remains poorly understood with some studies suggesting that biofeedback offers no advantage over the isolated pelvic floor muscle training.

Surface electromyography, as a diagnostic method for neurological disorders, is used to evaluate pelvic muscle activation patterns during muscle contraction in women with UI. Commercially available vaginal probes designed to record EMG from the pelvic floor muscles have numerous deficiencies in their design, such as problems with probe geometry, electrode size, location, and/or configuration. Many probe designs are prone to recording motion artifacts, crosstalk, and/or inappropriate EMG signals. The current art in the field indicates that their measurement accuracy and reproducibility are too low for the reliable characterization of the pelvic floor muscles conditions. There is therefore a need for an improved intravaginal EMG probe for use in research and clinical practice.

Electrical muscle stimulation (EMS) of pelvic floor muscles with intravaginal electrodes may help strengthening the urethral closure mechanism, which is necessary during SUI and inhibit spontaneous involuntary bladder contractions. The EMS has been found to improve strength and vascularity of various groups of muscles including external anal sphincter and mixed hemorrhoid disease. Nevertheless, some controversy exists on effectiveness of EMS as a stand-alone therapy for female SUI, which may be attributed by the inability to apply guided and targeted EMS.

Tactile Imaging is a medical imaging modality that translates the sense of touch into a digital image. The tactile image is a function of $P(x,y,z)$, where P is the pressure on soft tissue surface under applied deformation and x,y,z are coordinates where pressure P was measured. Functional Tactile Imaging translates muscle activity into dynamic pressure pattern $P(x,y,t)$ for an area of interest, where t is time and x,y are coordinates where pressure P was measured. Muscle activity may include: muscle voluntary contraction, involuntary reflex contraction, involuntary relaxation, or specific maneuvers (e.g Valsalva maneuver) [for further information see van Raalte H. Egorov V. Tactile imaging markers to characterize female pelvic floor conditions. Open Journal of Obstetrics and Gynecology 2015; 5: 505-515].

There is a need in imaging and quantitative assessment of pelvic floor muscles for the effective management of the disorders. Therefore is a need for improved methods and devices for vaginal tactile and electromyographic imaging, and guided female pelvic floor therapy in order to support a treatment therapy as well as to improve quality of life and reduce the negative psychological impact on patients needing pelvic floor treatment.

SUMMARY OF THE INVENTION

The objective of the present invention is to overcome the drawbacks of the prior art and to provide novel methods and devices for objective characterization of the female pelvic floor conditions.

Another objective of the invention is to provide methods and devices for objective characterization and real time visualization of contractile capabilities and electromyographic activities of pelvic floor muscles.

A further objective of the present invention is to provide methods and devices for objective visualization and real-time detection of damaged/weak pelvic floor muscles by measuring a tactile response and an electromyographic response during pelvic floor muscles contractions.

A further yet objective of the invention is to provide methods and devices for delivery of location-guided therapy of damaged/weak pelvic floor muscles.

Another objective of the invention is to provide methods and devices for location-guided therapy with an electrical stimulation for damaged/weak pelvic floor muscles.

A further yet objective of the invention is to provide methods and devices for objective diagnosis of a pelvic floor muscles disease by comparing an acquired tactile response and electromyographic response for a particular patient against respective normal values obtained from clinical data collected from a number of patients with known clinical status.

In embodiments, a method for vaginal tactile and electromyographic imaging and guided female pelvic floor therapy may include the steps of:

(a) providing a vaginal probe equipped with tactile sensors, plurality of electrodes which may be configured for use as electromyographic sensors or alternatively for electrical stimulation of pelvic floor muscles; and inserting that vaginal probe into a vagina along a vaginal canal with the aim of separating apart two opposing vaginal walls, (b) recording simultaneously a tactile response and an electromyographic response from at least one of said two opposing vaginal walls during pelvic floor muscle contraction, (c) determining target locations along said probe and therefore along said vaginal canal for application of location-guided therapy such as electrical stimulation, such locations may be determined based on absence of a predetermined level of a tactile response as well as on absence of a predetermined expected level of electromyographic response along said probe, and (d) applying the location-guided therapy to at least one or more of these selected target locations.

Examples of location-guided therapy may include location-specific electric muscle stimulation or location-specific drug injection, for example Botox®.

In embodiments, a vaginal probe for vaginal tactile and electromyographic imaging and guided female pelvic floor therapy may include:

a probe housing with a front portion suitably shaped or tapered for atraumatic insertion into a vaginal canal and for separating two opposing vaginal walls thereof, a plurality of tactile sensors forming together a tactile sensor array, these tactile sensors may be located over at least a portion of the probe housing in a predefined relationship of sensor positions to each other and to the probe housing; the tactile sensors may be appropriately selected and configured to record tactile response of pelvic floor muscles, a plurality of electrodes, wherein some or all of these electrodes may be configured to be used as electromyographic sensors forming together an EMG sensor array located over at least a portion of the probe housing in a predefined relationship of electrodes positions to each other and to the probe housing, the plurality of electrodes may be further selected and configured to record an electromyographic response of pelvic floor muscles during contraction of such muscles, at least one, some or all of the electrodes may be also configured to provide an electrical pulse stimulation at selected locations suitable for treatment of a pelvic floor dysfunction, and at least one or more reference electrodes configured to be attached to a skin near a vaginal canal.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows: "tactile sensor" is a sensor capable to measure an applied force averaged per sensor area or pressure; "electromyographic sensor" is a sensor capable to measure an electrical signal generated by a muscle relative to a reference sensor.

Figure 1:
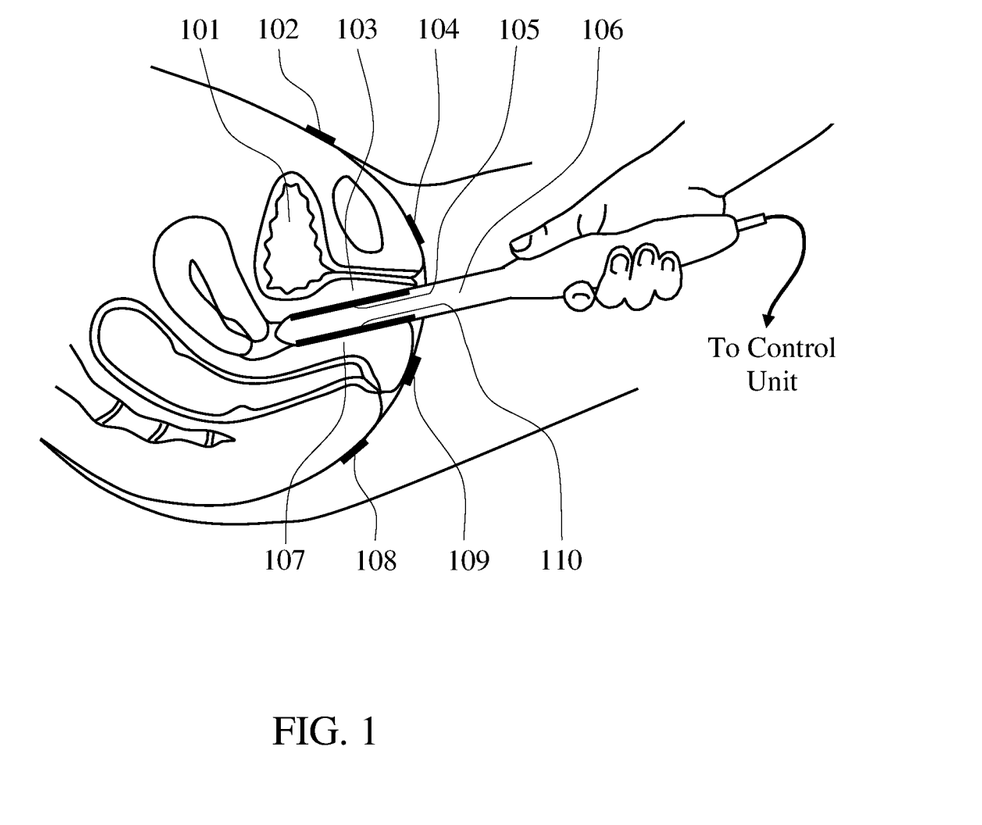
FIG. 1 illustrates a vaginal probe position after its insertion during recording of a tactile response and electromyographic response from two opposing vaginal walls; the same probe position is used for a location-guided therapy such as electrical muscle stimulation.

FIG. 1 illustrates position of a vaginal probe 106 after its insertion into vagina. The position of the probe is used for several purposes at the same location such as:
 a) recording of a tactile response and an electromyographic response from vaginal walls, and
 b) applying a location-guided therapy to selected location along vaginal walls for muscle stimulation.

Recording of a tactile response from two opposing vaginal walls in close contact with respectively an anterior 103 and a posterior 107 compartments may be provided by means of two tactile sensor arrays placed along the black lines 105 and 110 on both sides of the vaginal probe 106. Recording of an electromyographic response may be facilitated by providing one, two or more electromyographic sensor arrays along or close to the same black lines 105 and 110 on one or both sides of the vaginal probe 106. These tactile and electromyographic sensor arrays may be configured to record signals during pelvic floor muscle contraction as well as muscle at rest. Tactile measurements at muscle rest provide data for muscle tone, which may be considered as important characteristic of muscle conditions. Pelvic floor muscle contraction may be selected to be one of voluntary muscle contraction, involuntary muscle contraction, or muscle contraction during a Valsalva maneuver.

Further referring to FIG. 1, tactile and electromyographic sensor arrays 105 and 110 may be used to acquire signals from some, most or the entire length of a vaginal canal with linear resolution of at least of 5 mm or better. The tactile and electromyographic signal acquisition may be synchronized in time. Electromyographic sensors 110 and tactile sensors 105 may have the same spatial locations relative to a sensing surface of the probe 106 along lines 105 and 110. A location-guided therapy, such as an electrical stimulation, may be applied to vaginal walls at selected locations relative to reference electrodes 102, 104, 108 and 109. Electromyographic sensors 110 may be also used as stimulating electrodes relative to the reference electrodes 102, 104, 108 and 109. In embodiments, electrical stimulation pulses may be applied to vaginal walls at one or more of selected locations within vagina relative to at least one of reference electrodes 102, 104, 108 and 109 that may be placed on a skin surface in the vicinity of bladder 101, vagina and anus.

To accurately record tactile and electromyographic responses, the vaginal probe 106 must be held in place without any displacements by keeping the probe oriented in parallel to vaginal canal. The patient may be placed in a lithotomy position during the vaginal probe insertion, imaging and therapy. Furthermore, the patient may be asked to contract vaginal muscles to enable recording of tactile and electromyographic signals on a flat rigid surface 105 and 110 of the vaginal probe 106. The patient may further be asked to follow specific instructions from a medical professional for pelvic floor voluntary and involuntary (cough) muscle contraction as well as a specific maneuver (such as Valsalva).

Vaginal probe 106 may be made to have at least one of rectangular, ellipsoidal or circular cross-sections. In embodiments, the vaginal probe 106 may be shaped or tapered for an atraumatic insertion into vagina and may have a generally rectangular cross-section with rounded edges and angles, so that smaller sides of the vaginal probe 106 may be equipped with at least some of the tactile and electromyographic sensors. An electroconductive gel may be used with vaginal probe 106 during insertion into vagina.

Figure 2:
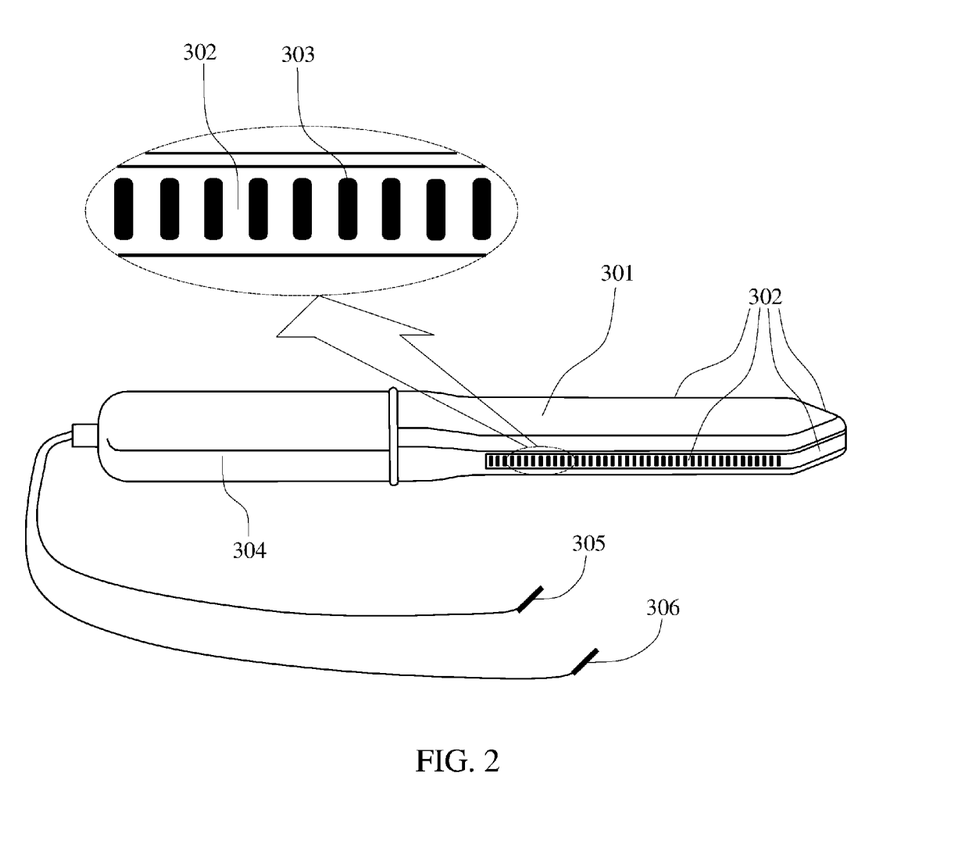
FIG. 2 presents an embodiment of a probe for vaginal tactile and electromyographic imaging, and location-guided female pelvic floor therapy.

FIG. 2 shows an exemplary embodiment of a vaginal probe 106 configured for vaginal tactile and electromyographic imaging, and location-guided female pelvic floor therapy. The vaginal probe may include a housing 301, a plurality of tactile sensors 302, a plurality of electrodes 303, a handle 304 as well as one, two, three or four reference electrodes 305, 306. The probe housing 301 may have a front portion suitably shaped or tapered for atraumatic insertion into a vaginal canal and for separating two opposing vaginal walls thereof. Such shape of the housing 301 may allow placing of at least some tactile sensors 302 and electrodes 303 forming electromyographic sensor arrays along two opposing sides capable to acquire tactile and electrical signals along a portion or the entire vagina from vaginal walls. The plurality of tactile sensors 302 forms together a tactile array located over at least a portion of the probe housing in a predefined and fixed relationship of individual tactile sensor positions to each other and to the probe housing 301. The tactile sensors 302 may be configured to record a tactile response of pelvic floor muscles with linear resolution of at least 5 mm or better. Further details of the tactile sensor array and the suitable probe design may be found in the U.S. Pat. No. 8,840,571 incorporated herewith in its entirety by reference.

At least some or all of the plurality of electrodes 303 may be configured to form an electromyographic sensor array located over at least a portion of the probe housing 301 in a predefined and fixed relationship of electrode positions to each other and to the probe housing 301. In embodiments, those electrodes that are used for the purposes of forming an electromyographic sensor array may be configured to record an electromyographic response of pelvic floor muscles during muscles contraction.

Furthermore, at least some or all of the plurality of electrodes 301 may also be used to form together an electrical muscle stimulation array configured to provide electrical pulse stimulation at selected locations for treatment of a pelvic floor dysfunction. Electrodes 303 and tactile sensors 302 may have the same or close spatial locations (one under another) relative to the sensing surface of the vaginal probe 106. For pelvic floor muscle assessment it is important to have synchronization of signals from electromyographic sensors and tactile sensors. Importantly, the same electrodes 303 may be used first as electromyographic sensors to record the electrical activities of the pelvic floor muscles and then can be switched to be used as stimulation electrodes. In one or both of these roles, electrodes 303 may be configured to operate relative to reference electrodes 305 and 306, which may be attached on skin surface in the vicinity of bladder, vagina and anus.

The vaginal probe 106 may be operably connected to a control unit, which may be configured to provide a clinician with a control interface for operating the vaginal probe 106 as well as a suitable display for visualizing all signals acquired during the procedure.

Figure 3:
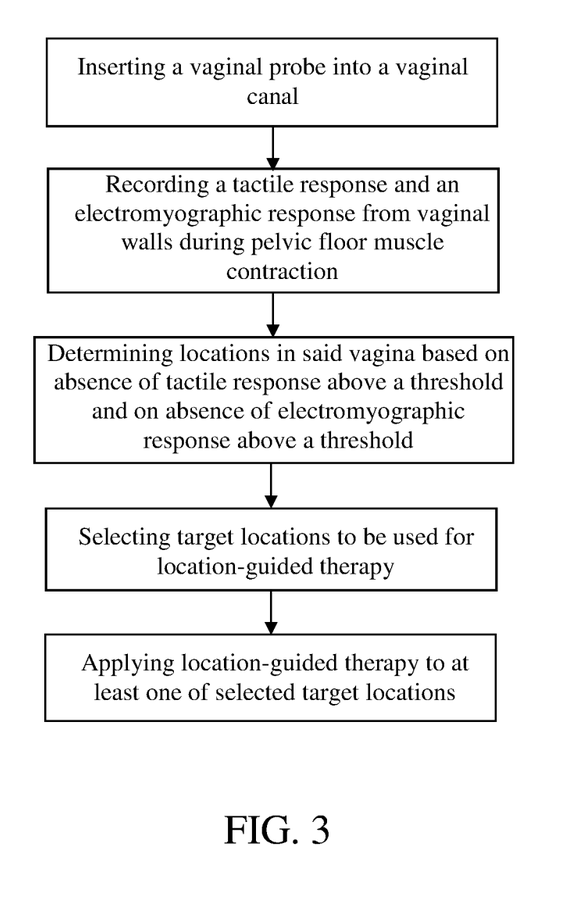
FIG. 3 is a flow chart illustrating an embodiment of a method for vaginal tactile and electromyographic imaging and location-guided female pelvic floor therapy.

FIG. 3 is a flow chart illustrating methods for vaginal tactile and electromyographic imaging and guided female pelvic floor therapy. One exemplary method may include the steps of:
  (a) inserting a vaginal probe equipped with tactile sensors and electrodes and reference electrodes along a vaginal canal to separate apart two opposing vaginal walls,
  (b) recording a tactile response and an electromyographic response from at least one of said two opposing vaginal walls during pelvic floor muscle contraction,
  (c) determining locations to deliver therapy in the vaginal canal based on presence or absence of tactile response above a predetermined tactile threshold and/or on presence or absence of electromyographic response above a predetermined EMG threshold along the vaginal probe. Such tactile and EMG thresholds may be determined in specific reference to a particular muscle and along the vaginal canal. In embodiments, the suitable levels for each of the tactile or EMG thresholds may be determined on a patient-specific basis or as a general guidance reference accumulated using recordings of many patients with known clinical status;
  (d) selecting at least one of locations to be used for delivering a location-guided therapy, and
  (e) applying the location-guided therapy at one or more of selected location.

In embodiments, the same probe position in vagina may be used for recording of tactile response and electromyographic response from vaginal walls, and for applying location-guided therapy to vaginal walls for muscle stimulation. Further in embodiments, recording of tactile response and electromyographic response may have spatial resolution of at least 5 mm along a portion or the entire vaginal canal. Tactile response and electromyographic response may be recorded from at least one of pelvic floor muscles such as puborectalis, pubococcygeus, pubovaginal, puboperineal, levator plate and ilicoccygeal. Muscle contraction strength may be determined from tactile response recording in a form of a dynamic increase of a pressure value on a surface of the vaginal probe. Determination of a muscle resting tone from recorded tactile response without pelvic floor muscle contraction may also be used to determine the baseline of muscle relaxation. Importantly, determination of locations along the vaginal canal for delivery of location-guided therapy may be based on a) clinically established threshold for a minimally acceptable tactile response for specific a pelvic floor muscle, and/or b) clinically established threshold for a minimally acceptable electromyographic response for a specific pelvic floor muscle.

Location-guided therapy may include application of electrical stimulation pulses to at least one of the selected locations relative to at least one of reference electrodes placed on a skin surface in the vicinity of bladder, vagina and anus. Location-guided therapy using electrical stimulation pulses may be used to treat at least one of pelvic floor dysfunctions such as overactive bladder, urinary incontinence, uncoordinated muscle contractions, fecal incontinence and pelvic organ prolapse.

Figure 4:
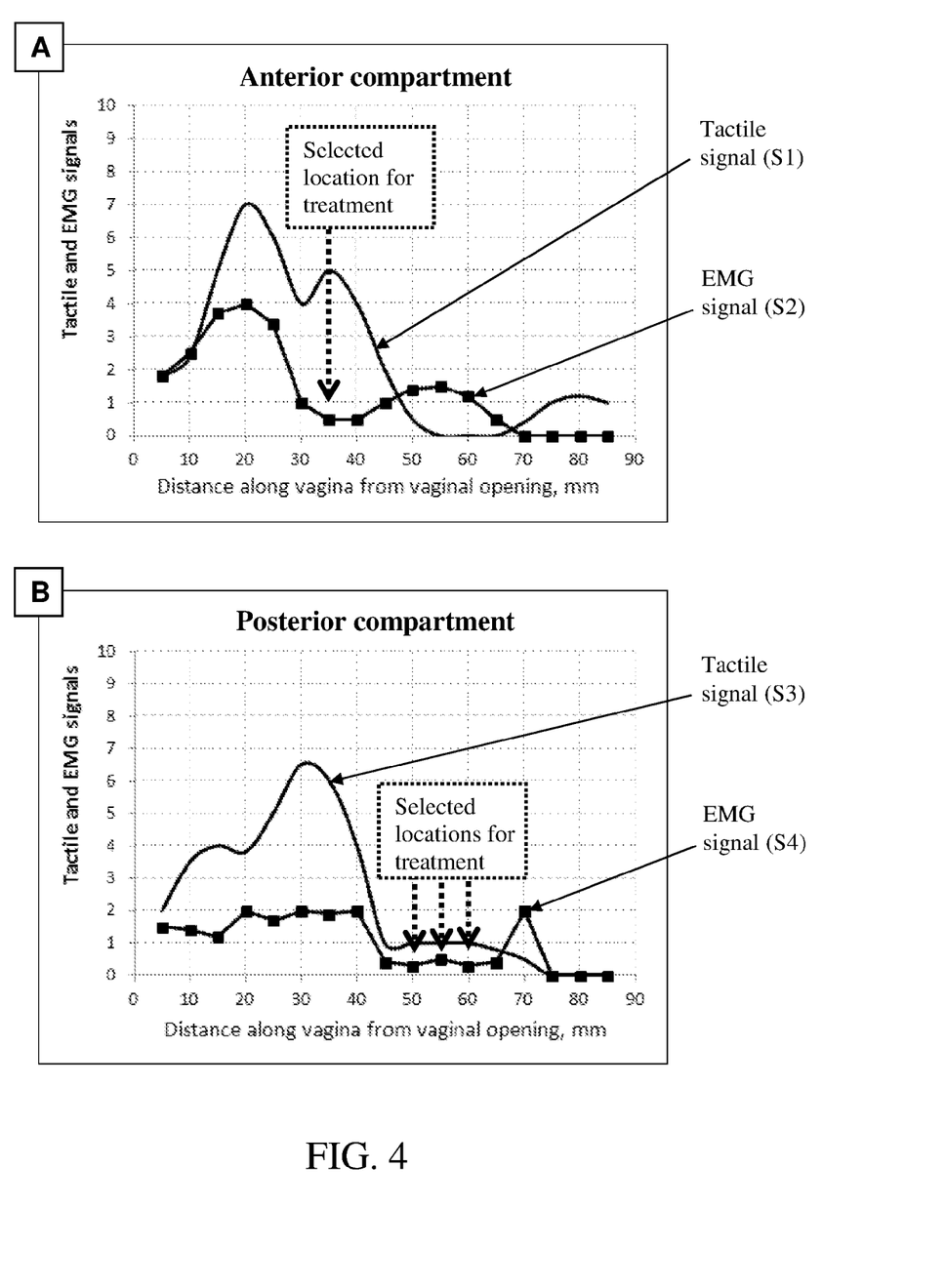
FIG. 4 illustrates the use of a tactile response and an electromyographic response for selecting the locations in anterior (A) and posterior (B) compartments for location-targeted pelvic floor therapy.

FIG. 4 illustrates an example of using tactile responses (S1 and S3) and electromyographic responses (S2 and S4) for anterior (A) and posterior (B) compartments of vagina. In this example, electromyographic (EMG) signal at 35 mm in FIG. 1A is significantly lower than the tactile response at the same coordinate (35 mm); and therefore this anterior location can be selected for location-guided therapy treatment. An operator may observe the signals shown in FIG. 4 in real time. To apply electrical stimulation at 35 mm to anterior compartment, the operator may select this location (35 mm) using a computer control interface and initiate therapy delivery at this location while keeping the vaginal probe 106 steadily at the same position. In this case, only one electrode located at 35 mm mark will participate in electrical stimulation applied to anterior muscle in this location relative to a reference electrode placed on skin above the bladder. Further, the operator may observe that EMG signals at 50-60 mm in FIG. 1B are significantly lower than the tactile response and expected level of electromyographic response; these posterior locations (50 mm, 55 mm and 60 mm) may also be selected for location-guided therapy. To apply electrical stimulation at 50-60 mm to the posterior compartment, the operator may select these locations (50 mm, 55 mm and 60 mm) using the same computer control interface and allow electrical stimulation to be initiated while keeping the vaginal probe 106 steady in the same position during the therapy. Only electrodes at 50 mm, 55 mm and 60 mm will therefore be activated for electrical stimulation applied to posterior muscle in specified locations relative to one or more reference electrode placed on skin behind the rectum.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for vaginal tactile and electromyographic imaging and applying a location-guided female pelvic floor therapy, said method comprising the steps of:
  (a) providing a vaginal probe equipped with a plurality of tactile sensors and a plurality of electrodes including at least one external reference electrode,
  (b) inserting said vaginal probe into a vagina along a vaginal canal to separate apart two opposing vaginal walls,
  (c) recording simultaneously a tactile response and an electromyographic response from at least one of said two opposing vaginal walls during pelvic floor muscle contraction, said electromyographic response is recorded between at least one electrode on said probe and said at least one external reference electrode positioned on a skin of said female in a vicinity of said vaginal probe,
  (d) determining one or more target locations along said probe in said vaginal canal for delivery of said therapy, said locations are selected based on absence of tactile response above a predetermined tactile threshold and based on absence of electromyographic response above a predetermined electromyographic threshold, (e) applying said location-guided therapy to said selected one or more target locations.

2. The method as in claim 1, wherein said step (c) of recording said tactile response and said electromyographic response from vaginal walls and step (e) of applying said location-guided therapy to said vaginal walls are conducted at the same position of said vaginal probe.

3. The method as in claim 1, wherein said step (c) of recording of said tactile response and said electromyographic response is conducted with a spatial resolution of at least 5 mm or better along a portion of or said entire vaginal canal.

4. The method as in claim 1, wherein said step (c) further including recording said tactile response and said electromyographic response from at least one of pelvic floor muscles selected from a group consisting of a puborectalis muscle, a pubococcygeus muscle, a pubovaginal muscle, a puboperineal muscle, a levator plate muscle, and a ilicoccygeal muscle.

5. The method as in claim 1, wherein said step (c) further comprising determining a muscle contraction strength using said tactile response in a form of a dynamic increase of a pressure value on said probe housing.

6. The method as in claim 1, wherein said step (c) further comprising determining a muscle resting tone from said tactile response without said pelvic floor muscle contraction.

7. The method as in claim 1, wherein in said step (d) said predetermined tactile threshold in based on recordings from a plurality of subjects with known clinical status.

8. The method as in claim 1, wherein in said step (d) said predetermined electromyographic threshold in based on recordings from a plurality of subjects with known clinical status.

9. The method as in claim 1, wherein said step (e) further including applying electrical stimulation pulses to at least one of said selected locations.

10. The method as in claim 1, wherein said step (e) is applied to treat at least one of pelvic floor dysfunctions selected from a group consisting of an overactive bladder, a urinary incontinence, an uncoordinated muscle contractions, a fecal incontinence, and a pelvic organ prolapse.

* * * * *